United States Patent [19]

Fennell

[11] 4,002,967

[45] Jan. 11, 1977

[54] ANNULAR EDDY CURRENT TEST COIL WITH MAGNETIC LAMINATIONS ADJACENT A LIMITED CIRCUMFERENTIAL EXTENT

[75] Inventor: S. Reed Fennell, Kittanning, Pa.
[73] Assignee: Aluminum Company of America, Pittsburgh, Pa.
[22] Filed: Aug. 1, 1975
[21] Appl. No.: 601,203
[52] U.S. Cl. .................................. 324/40; 336/234
[51] Int. Cl.² ........................................ G01R 33/12
[58] Field of Search .................. 324/37, 40, 34 R; 336/233, 234

[56] References Cited

UNITED STATES PATENTS

| 2,351,595 | 6/1944 | Bindschelder | 324/34 R |
| 3,500,181 | 3/1970 | Jackson | 324/37 |
| 3,518,533 | 6/1970 | Arnelo | 324/40 |
| 3,916,302 | 10/1975 | Madewell | 324/37 |

FOREIGN PATENTS OR APPLICATIONS

| 914,595 | 10/1946 | France | 324/37 |
| 991,890 | 5/1965 | United Kingdom | 324/40 |

Primary Examiner—Robert J. Corcoran
Attorney, Agent, or Firm—Elroy Strickland

[57] ABSTRACT

A magnetic pole and coil assembly for concentrating eddy currents in a limited peripheral portion of a metal product being examined by the assembly. The assembly comprises at least one winding adapted to produce a magnetic field when supplied with alternating electrical current, and laminations of high permeability magnetic material disposed closely adjacent a portion of the winding to concentrate the magnetic field in the vicinity of the magnetic laminations.

7 Claims, 4 Drawing Figures

ANNULAR EDDY CURRENT TEST COIL WITH MAGNETIC LAMINATIONS ADJACENT A LIMITED CIRCUMFERENTIAL EXTENT

BACKGROUND OF THE INVENTION

The present invention relates generally to eddy current test coil structures, and particularly to a pole and coil assembly adapted to concentrate magnetic lines of force in a limited area of the coil to thereby concentrate the resulting eddy currents produced in a metal product by the concentrated lines of force as the metal product is directed through the coil.

Heretofore, in the art of continuously examining elongated metal product directed past an examining station, the practice has usually been to direct the product through a circular coil or coils designed to induce eddy currents in the product in a uniform manner. The magnetic lines of force generated by the coil or coils enter the product in a generally uniform manner so that the product, or at least the periphery thereof, is uniformly examined.

Such a test coil is shown schematically in U.S. Pat. No. 3,735,084, issued on May 22, 1973, in the name of John M. Urbanic et al. The coil is employed to receive and pass therethrough a tubular product formed from a strip of metal welded along aligned abutting edges thereof. The coil and associated circuitry in this patent is adapted to examine the wall and the seam weld of the product and to reject any portions thereof having a defect. It has been found, with the use of such coils, that tubing having a structurally sound wall and seam weld has been rejected on the basis of dents, scratches or other surface discontinuities on the wall thereby generating, unnecessarily, substantial amounts of a scrap material. On the other hand, at the same time, such a search coil will function to accept and pass, as good tubing, tubing lengths having extremely small discontinuities or "microleaks" in the seam weld, which lengths should have been rejected. It can be appreciated that if the welded tube is employed in a heat exchange unit, in which the tube contains and directs fluids therethrough under pressure in the heat exchanging process, any minute crack or discontinuity in the tube weld will disable the complete unit.

Another approach of the art to examining traveling, elongated metal product is the use of eddy current probes, such as shown in the Lorenzi et al. U.S. Pat. No. 3,495,166. Such probes tend to concentrate the eddy currents inducing magnetic field to such an extent that defects and discontinuities lying outside the concentrated field are missed. In the Lorenzi et al patent, for example, the probe is designed to search for defects having a dimension that is substantial in one direction only.

Thus, the problem of adequately examining the longitudinal weld of seam welded product for even the minutest discontinuity, without the attendant result of rejecting otherwise good and sound tubing, has not been solved by the type of test coil that simply surrounds the tubing and uniformly directs magnetic lines of force into the tubing wall, or by the probe that examines a very restricted area of a product or searches for a particular type of defect only.

Other U.S. patents showing probe and/or product encircling test coils for examining elongated product are Knerr et al. No. 2,124,579, Paivinen No. 2,744,233, Datt et al., No. 2,980,848, Hochschild No. 3,056,081, Quittner No. 3,273,055, Brown No. 3,395,339 and Puidak No. 3,449,661. In the Datt et al. patent, a pair of excitation and sensing coils are shown separated by a partition of "Mu Metal". The Mu Metal, with the coils, encircles the workpiece to be examined so that a magnetic field is generated and directed uniformly into the entire periphery of a workpiece to be tested.

FIG. 12 of the above Knerr et al patent shows a device for sensing flaws in tubular product using two spaced apart primary excitation windings completely surrounding the product, and secondary sensing windings located intermediate the excitation windings. The excitation windings generally uniformly produce eddy currents in the product, while the sensing windings detect flaws in the product only in the area of the sensing windings. In addition, the detection windings are shown shielded from the excitation windings by laminations of iron, copper or the like.

In addition, Flaherty et al. U.S. Pat. No. 3,430,134 discloses the use of three coils to track and test seam welds in pipe, the coils being magnetically isolated from each other to increase sensitivity to the weld location. Further, the coils are elongated in the direction of the weld so that an integrating and averaging effect is provided, which effect reduces sensitivity of the probe to minor discontinuities in the weld.

BRIEF SUMMARY OF THE INVENTION

Briefly, the present invention overcomes the deficiencies of prior product encircling and probe type coil arrangements by using a simple and inexpensive magnetic pole structure located adjacent a limited peripheral area of a typical annular coil structure (designed to receive and pass elongated product therethrough) to direct and concentrate the magnetic lines of force generated by the coil structure in the area of the magnetic structure. In this manner, the magnetic field generated by the coil structure to induce eddy currents in longitudinally welded product, for example, will be concentrated in the area of the longitudinal weld and for a limited distance on each side of the longitudinal weld, as provided by the physical extent of the pole structure. This limited distance that the concentrated field extends on each side of the weld is particularly important since the weld seam itself does not travel in a perfectly straight line, but rather tends to wander somewhat. By being able to measure an area on each side of the seam, the magnetic structure of the present invention does not need to track the seam, as is done in the above Flaherty et al. patent.

Such a structure, using a matched pair of annular coils connected to an associated detecting and coil energizing circuit, has been highly successful in discovering minute, microleaks in the seam welds of tubular product without detecting dents and other surface discontinuities in the product lying outside the inspected area. In this manner, sound tubing, with a soundly welded seam, is not rejected because of such surface discontinuities thereby greatly reducing the amount of scrap material produced in the process of examining tubing.

THE DRAWINGS

The invention, along with its objectives and advantages, will be best understood from consideration of the following detailed description taken in connection with the accompanying drawings in which.

PREFERRED EMBODIMENT

Figure 1:
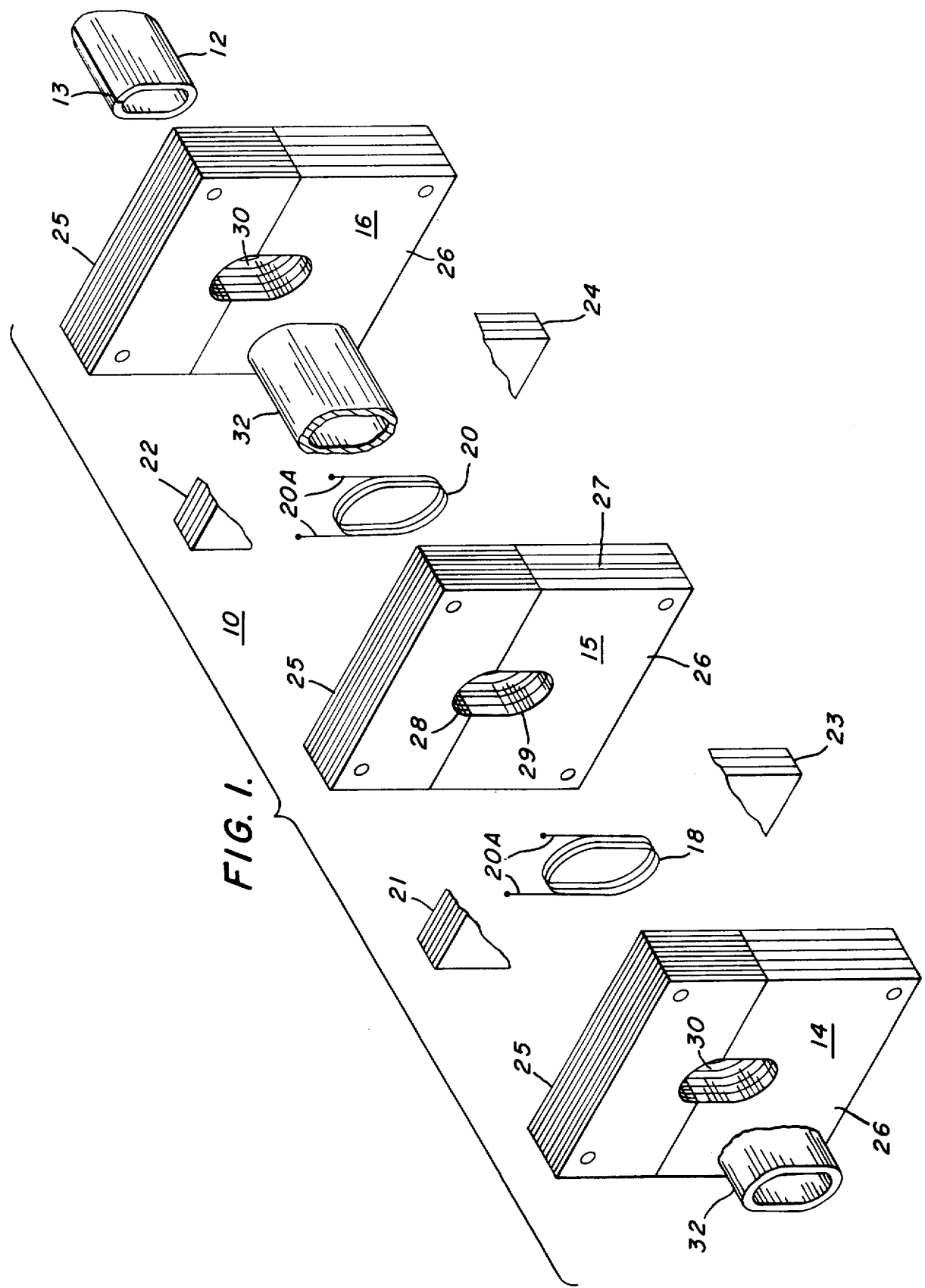
FIG. 1 is an exploded view of the pole and coil assembly of the invention.

Referring now to the drawings, FIG. 1 thereof shows an exploded view of the pole and coil assembly of the invention, the assembly being generally designated by numberal 10. In addition, the end portion of an elongated tubular product 12 is shown in FIG. 1, the product having a longitudinally extending, seam weld 13 to be inspected by the structure 10 and its associated circuitry (not shown).

Figure 2:
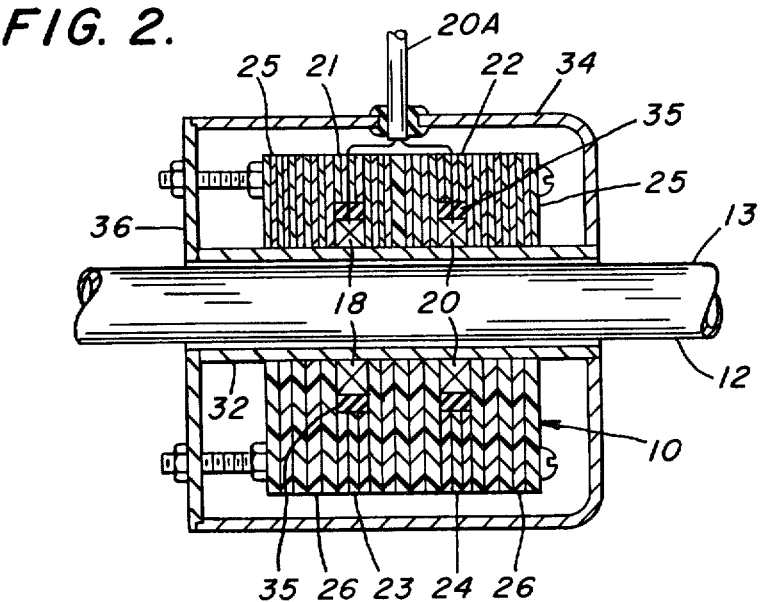
FIG. 2 is a longitudinal section of the assembly of FIG. 1.

More particularly, assembly 10 comprises, as shown in FIGS. 1 and 2, three narrow pole structures 14, 15, and 16 physically separated by two annular and relatively flat coil windings 18 and 20 and spacer laminations 21 to 24. The windings 18 and 20 have leads 20A for connecting to a detecting (balanced bridge) circuit and source of electrical energy (not shown). The two windings are a matched pair that, when energized with alternating or pulsating electrical current, function to both excite the product to be inspected with eddy currents and to sense any interruption of eddy current flow in the product by being respectively connected in two legs of the balanced bridge circuit.

Each of the pole structures has an upper portion 25 made of a high permeability magnetic material, such as laminations of silicon steel, though other magnetic materials may be used. When the pole structures and windings are placed together, as shown in FIG. 2, the magnetic portions 25 of the pole structures, which include spacer laminations 21 and 22, occupy a limited peripheral or arc portion of the windings. In the drawings, the portion of each coil occupied by pole 25 is about one-fourth of the total periphery of the coil.

In order to maintain the integrity of the pole structures and assembly, a lower pole portion 26, corresponding in configuration to the upper portion 25 is included, the lower portion being made of non-magnetic material, such as a glass fiber material. In FIGS. 1 and 2, each lower portion 26 is shown as a laminated structure, though a solid structure may be employed. Also, the lower portion 26, along with the spacer laminations 23 and 24, can be eliminated altogether as long as the integrity of the pole structures and windings is maintained. In use, the pole structures and assembly are packaged in a manner that will protect the components of the assembly, such as depicted in FIG. 2, as described in detail hereinafter.

To secure the upper and lower portions 25 and 26 of the poles together, one or more very thin laminations 27 common to the upper and lower portions can be used, only one such lamination being shown in FIG. 1 in pole 15. Lamination 27 is made of a non-magnetic material so as not to offer a path for conducting magnetic flux away from the upper magnetic portion 25 of the structures, and is very thin so as not to impede the flux path in the upper magnetic portion of the pole, though, in FIGS. 1 and 4, the lamination is depicted being relatively thick for purposes of illustration.

As indicated in FIG. 1, the laminations of the magnetic and non-magnetic structures 25 and 26 of each pole structure 14, 15 and 16 have a configuration that provides an opening 30 for passing therethrough the product to be tested. Individually, 25 and 26 can have respective recesses 28 and 29 which extend inwardly from one edge of each lamination and structure. When the laminated structures 25 and 26 are placed together in the manner of FIG. 1, with the recesses facing each other, the opening 30 is formed. The recesses and opening are sized to pass therethrough tubular product 12, for example, and to receive, preferably, a tubular bushing or liner 32 dimensioned to pass the tubular product, and constructed to protect the pole structures 14 to 16 and windings 18 and 20 as the product travels therethrough. The liner thus extends completely through the structure 10 and through a housing structure 34, as shown in FIG. 2. The liner is made from a non-magnetic material so as not to affect the magnetic fields (as described hereinafter) produced by windings 18 and 20.

Figure 4:
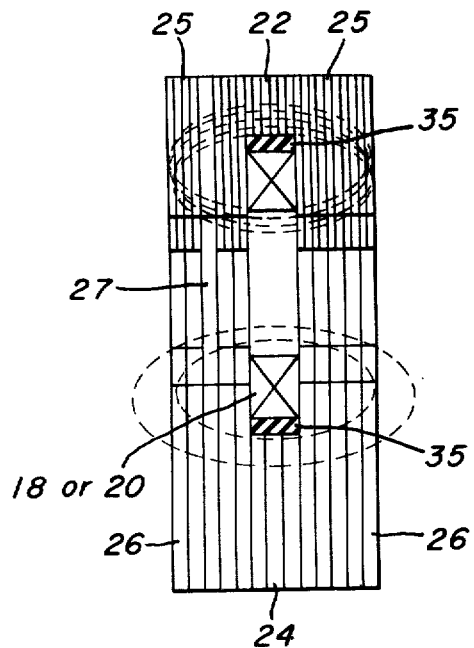
FIG. 4 shows the winding of FIG. 3 in combination with two magnetic pole structures to provide concentration of the magnetic lines of force generated by the winding in accordance with the principles of the present invention.

As best seen in FIG. 2, the spacer laminations 21 to 24 occupy the spaces between the poles 14, 15 and 16, and surround the periphery of the windings 18 and 20. The laminations of the upper spacers 21 and 22 are, like the laminations of poles 25 made of high permeability magnetic material which provides a good path for conducting magnetic flux between the magnetic material of the poles, as indicated in FIG. 4. The lower spacer laminations 23 and 24, like lower pole portions 26, are made of a non-magnetic material, which can be the same material as the lower pole portions. Together, the spacer laminations accommodate windings 18 and 20 between pole structures 14 and 16.

Since the spacer laminations must accommodate windings 18 and 20 between the pole structures, the spacer laminations must provide openings that are larger than the openings 30 provided by the recesses of laminations of 25 and 26. In addition, as shown in FIGS. 2 and 4, the spacer openings preferably also are sized to accommodate a rubber compound and sealant 35 located around the windings to tightly secure, in a vibration free manner, the windings between liner 32 and the spacer laminations.

As further shown in FIG. 2, the laminations of 21 to 26 can be bolted together and to a front plate 36 of housing 34 to permit these structures and windings to be disposed and sealed in a potting compound (not shown) contained within the housing. Such a compound and housing serve to provide a rugged sensing head unit particularly suitable for the rough conditions encountered on line with apparatus for forming and welding tubular product from strip material in a continuous, high speed manner. In addition, the potting compound adheres to liner 32 to retain it in housing 34.

In practice, it has been found that the resolution, and thus the ability of the coil assembly 10 to detect minute discontinuities in a product under test, is greatly enhanced by using narrow width pole structures 25, i.e. pole structures that are on the order of 1/16 of an inch thick (as viewed in FIGS. 2 and 4). The reason for this is that (again) the magnetic field is highly concentrated by the narrow pole structures and in the area of the product examined by the field adjacent the pole structures.

In the process of making a tubular product, the contour or cross sectional configuration thereof may be changed from a generally circular shape to that of the somewhat ovate shape of tube 12 of FIG. 1. If this change in configuration occurs before the location at which the tube is examined, i.e., at the location of the testing assembly 10 of the invention, the annular configurations of liner 32 and coils 18 and 20 of the assembly and the openings 30 in pole structures 14 to 16 of the assembly are shaped to conform to the configuration of the product 12 being examined.

Figure 3:
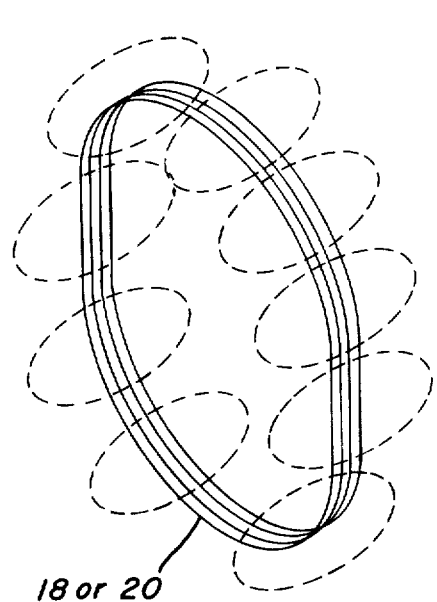
FIG. 3 is an elevational view of an annular winding showing generally the uniform location of the magnetic lines of force generated by the winding.

In the operation of a test coil encircling a metal product to be examined by the coil (and its associated circuitry), the coil, when energized by a suitable alternating or pulsating source of electrical energy, generates magnetic lines of force in the manner shown in dash outline in FIG. 3, i.e., in a generally uniform manner about the annular configuration of the structure, the lines of force extending in planes generally parallel to the axis of coil. These magnetic lines of force, which change direction with each change of the energizing cycle, induce eddy current flow in any metal located in or adjacent the center of the coil or in the process of being axially directed through the coil. If the metal is centered or near center in the coil, the eddy currents induced in the metal will be generally uniformly located in the metal.

As indicated earlier, if only a portion of the item being examined is critical, such as the weld seam in a longitudinally welded product, coils that generate uniform magnetic fields and eddy current flow tend to miss small discontinuities or microleaks in the weld area while simultaneously signaling the rejection of structurally sound product by sensing harmless surface deformities.

The coil and pole structures of FIGS. 1 and 2 solve this problem by directing and concentrating the magnetic lines of force generated by the coils 18 and 20 in the manner shown in FIG. 4. More particularly, the lines of force (in dash outline) are pulled into the magnetic material of cores 25 to be concentrated therein and in the vicinity of cores and away from the area of the non-magnetic material 26, shown in phantom outline in FIG. 4. In this manner, when a metal workpiece or product, such as welded tube 12, is directed through coils 18 and 20 and past cores 25, eddy current activity in the workpiece or product is concentrated in the longitudinal portion of the product closest the cores 25 and concentrated magnetic field. If the weld 13 of product 12 travels in close proximity to the cores 25, as indicated in FIGS. 1 and 2, the eddy current activity in the product is concentrated in the weld area and in longitudinal extending areas adjacent the weld area, the width of these areas and eddy current activity therein depending upon the width of the cores 24.

With the concentration of eddy current activity in the locality of a critical area, such as weld 13, any minute crack or discontinuity (as well as a large crack or discontinuity) is easily sensed by coils 18 and 20 and their associated circuitry when such discontinuities interrupt and redirect eddy current flow around the discontinuity. Eddy currents generate their own magnetic fields, which are sensed by the coils, so that, with the interruption and redirection of the eddy currents, the coils and circuit function to sense the resulting change in the magnetic field. This sensing function is effected without being affected by any surface deformities on the product since the magnetic field and eddy current activity is minimal in the areas removed from the area of cores 25 and spacer laminations 21 and 22. Hence, minimum scrap is generated on the basis of such deformities.

While the invention has been described in terms of a preferred embodiment, the claims appended hereto are intended to encompass all embodiments which fall within the spirit of the invention.

What is claimed is:

1. A magnetic pole and coil assembly for limiting and concentrating eddy currents in a peripheral arc portion of a metal product, the assembly comprising
    at least one annular winding electrically connectable to a source of alternating or pulsating electrical energy, and adapted to produce magnetic flux capable of inducing eddy currents in a metal product when the winding is energized by said source, said winding being adapted to have the product pass therethrough and
    laminations of a magnetic material disposed adjacent a limited circumferential portion of said winding for concentrating and limiting the magnetic flux produced by said winding in and to the area of the magnetic laminations, and thereby being effective to increase the density of the flux and eddy currents in a predetermined arc portion of a metal product when the metal product is directed past the laminations and through the winding in a rapid, continuous manner and in close proximity but spaced relation to the laminations and winding.

2. The assembly of claim 1 in which a structure made of non-magnetic material is located adjacent the remaining circumferential portion of the annular winding and in a position opposed to that of the magnetic laminations.

3. The assembly of claim 2 in which the magnetic laminations and the non-magnetic material have a configuration that provides an opening capable of passing therethrough metal product to be examined by the assembly.

4. The assembly of claim 2 including a second annular winding connectable to a source of electrical energy, and spaced from the winding of claim 1 by the magnetic laminations and the non-magnetic material.

5. The assembly of claim 4 including a tubular liner made of non-magnetic material extending between the windings and between the laminations and non-magnetic material, said tubular liner being adapted to receive and pass elongated product therethrough.

6. The assembly of claim 2 in which the non-magnetic structure is in the form of laminations made from a non-magnetic material.

7. The assembly of claim 6 in which the magnetic and non-magnetic laminations are held together by fastening means and at least one, common, non-magnetic lamination, said fastening means securing the laminations, including the common lamination, together.

* * * * *